United States Patent [19]

Bolth

[11] 4,120,888

[45] Oct. 17, 1978

[54] PREPARATION OF CHLORINE-SUBSTITUTED CHLOROFORMATES

[75] Inventor: Franklin Anderson Bolth, Baltimore, Md.

[73] Assignee: Minerec Corporation, New York, N.Y.

[21] Appl. No.: 872,573

[22] Filed: Jan. 26, 1978

[51] Int. Cl.$^2$ ............................................. C07C 68/02
[52] U.S. Cl. .................................................... 260/463
[58] Field of Search ......................................... 260/463

[56] References Cited

U.S. PATENT DOCUMENTS

| 2,397,630 | 4/1946 | Strain ................................. | 260/463 |
|---|---|---|---|
| 2,476,637 | 7/1949 | Strain et al. .......................... | 260/463 |
| 2,732,914 | 1/1956 | Holden ................................ | 260/463 |
| 2,820,809 | 1/1958 | Frevel et al. ........................ | 260/463 |
| 2,820,810 | 1/1958 | Frevel et al. ........................ | 260/463 |
| 3,966,786 | 6/1976 | Rozsa et al. ......................... | 260/463 |
| 4,039,569 | 8/1977 | Bell et al. ............................ | 260/463 |

FOREIGN PATENT DOCUMENTS 1,179,922  10/1964  Fed. Rep. of Germany ........... 260/463

OTHER PUBLICATIONS

J. I. Jones et al., *J. Chem. Soc.*, 1957, pp. 2735–2743, "The Reaction of Carbonyl Chloride with 1:2 Epoxides".

M. S. Malinovskii, Chem. Abstracts, 48:2580c.

*Primary Examiner*—Lewis Gotts
*Assistant Examiner*—Molly C. Eakin
*Attorney, Agent, or Firm*—James J. Burke, II

[57] ABSTRACT

Chloroethyl, chloropropyl, and other chlorine-substituted chloroformates are manufactured by reaction of phosgene with appropriate epoxide compounds, in a new manner, that results in very high yields of product in a continuous process. The process requires the use of activated carbon as a stationary catalyst, a circulating load of pre-formed product as diluent, and operating temperatures in the range of 60° to 125° C. preferably 75° to 115° C.

7 Claims, No Drawings

PREPARATION OF CHLORINE-SUBSTITUTED CHLOROFORMATES

BACKGROUND OF THE INVENTION

The present invention relates to the preparation of chlorine substituted chloroformates. More particularly, the invention relates to preparing such compounds in a process that is continuous and has high yields and purity. The process is described with particular reference to the preparation of 2-chloroethyl, 2-chloroisopropyl, 3-allyloxy 1-chloroisopropyl, and 3-phenoxy 1-chloroisopropyl chloromates. While it is not believed to be so limited, certain reservations are expressed with respect to across-the-board application to all chlorine-substituted compounds of the same type.

These compounds are useful in the preparation of flotation reagents of the xanthogen formate type, and in other organic syntheses. It should be noted at the outset that both reactants and products are both toxic and corrosive, and must be handled and used with appropriate precautions.

Chloroformates are the reaction product of phosgene (carbonyl chloride) and organic alcohols, oxides, and some carbonyls. Insofar as known, the reactions are always highly exothermic, and are plaqued by low yields (with a variety of by-products) requiring elaborate purification procedures. Most prior art teachings are restricted to one or a small group of compounds, and this is in accord with my own and coworker's experience, in that what works for one set of reactants will not necessarily work with even a closely related set. An exception to this is the patent of Strain et al., U.S. Pat. No. 2,476,637. There, reaction under conditions of total reflux is disclosed, and while this is believed to be appropriate for the specific system disclosed, it would be very inadequate for many of the long list of proposed substitute reactants. The following patents are considered more limited and, hence, more typical.

U.S. Pat. No. 2,820,809 and 2,820,810 of Frevel et al. disclose manufacture of 2-chloroethyl chloroformate and 2-chloro-1-methylethyl chloroformate, respectively. In the first case, reactants are in the gaseous state, phosgene being reacted with ethylene oxide in the presence of HCl vapor as catalyst. In the second case, liquids are used at temperatures near 0° C., propylene oxide and phosgene are reacted, again with added HCl. In both cases product is purified by distillation, and yield is about 50–55%. Of course, the need to continuously add the catalyst, plus removal of same, insofar as possible, from the product, is a significant cost factor.

More recently, in U.S. Pat. No. 4,039,569 Bell et al., assigned to the same assignee as the instant application, a continuous process of making methyl chloroformate by reacting liquid methanol with phosgene in a large, circulating load of pre-formed chloroformate, at 15°–16° C. is disclosed. Product at 98% pure, and yields over 80% are reported. Two points are of interest with this process: First, it is carried out without any catalyst at all. Second, and perhaps more important is exemplifying the state of this art, the same general process could not be employed to produce ethyl chloroformate with any degree of success.

The stoichiometry of the reaction between phosgene and epoxides has been studied to a limited extent (Jones, J. Chem. Soc. 1957, 2735–43, Chem. Ab. 51, 16433b). All reactions were carried out at 10° C. with pyridine present, over 1.25 hours, followed by distillation. Generally, it was determined that chloroformates resulted from 1:1 molar proportions, but chloroalkyl carbonates resulted if the epoxide quantity was doubled. Yield was apparently about 80%, but purity was not reported. Fifty percent yields with ethylene oxide and propylene oxide were reported earlier by Malinovskii et al. with ethylene bromide as solvent, at 0° C., (Chem. Ab. 48, 2580C).

It is at least possible that some confusion has resulted from prior workers calling true epoxy or epoxide compounds by the more generic "oxide". As used herein, epoxide is intended to mean the true epoxy structure, wherein the oxygen is bound to two separate atoms that are otherwise joined.

OBJECTS OF THE INVENTION

A general object of the present invention is to provide an improved process for producing chlorine-substituted chloroformates.

More particular objects of the present invention are to produce chloroethyl and chloroisopropyl chloroformates in a continuous process, with a high yield, without added solvents, and at a substantial rate.

Still further objects of the present invention are to effectively catalyze the reaction of phosgene and epoxides, to use a permanent catalyst, and to provide means of cooling it and the reaction mixture, to obtain chlorine-substituted chloroformates at +95% yield and purity.

DESCRIPTION OF EMBODIMENTS

The reaction of phosgene with an epoxide is written as follows:

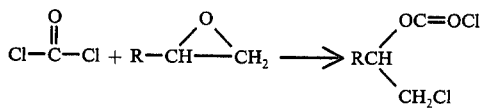

In this equation, R may be hydrogen, lower alkyl, or another organic group.

As noted supra, prior workers have used solvents, low temperatures and continually renewed catalysts, and still suffer low yields.

In one aspect, the present invention is based on the discovery that Reaction 1 is catalyzed to a remarkable degree by activated carbon, in either pellet or powder form. Even more surprising, the catalyst does not appear to lose activity with time (e.g. a 10-kilogram run).

A second and more important aspect of the invention is the discovery that reaction 1 can be run substantially to completion (with the carbon catalyst) at temperatures an order of magnitude higher than contemplated by prior workers, provided the heat of reaction is effectively absorbed. The higher temperature, of course, has the expected effect on rate of reaction. Necessary temperature control is effected by using a large quantity of the final product as a temperature-moderating medium, so that the concentration of reactants at any one time or point is kept low. This, plus relatively moderate cooling, serve to maintain the reaction temperature in the desired range of 60° to 125° C.

It is to be noted that prior workers with epoxides used freezing temperatures both to minimize byproducts and to keep the reaction under control by preventing boiling-off of solvents and reactants. Further, in the better-known reactions with alcohols, a certain amount of HCl is necessarily produced, and its vaporization removes some of the reaction energy. Thus, in the present invention, the absence of HCl either as a byproduct or catalyst would seem to worsen control problems, but the use of the permanent carbon catalyst, high reaction temperatures and circulating chloroformate coolant combine to produce an improved and, more important, continuous process.

Initial catalyst testing was done in a small glass reactor provided with a gas diffuser, a thermometer, a stirrer, an electric heating mantle and an ice water cooled condensor. One gram mol of phosgene was diffused into 1.1 gram mols of propylene epoxide in about 3 hours. In the reactions with active catalysts, it was possible to hold the reaction temperature between 28° and 34° C., but in the less successful trials, phosgene accumulated and brought the temperature down to 20° C. After mixing, all reactants stood overnight. The volatiles were removed by a vacuum treatment, the catalyst was removed by filtration, and the chloroformate was washed once with cold water and dried. The products were assayed and the yield determined against the quantity of phosgene added. Results are set forth in Table I hereinbelow, and the superiority of carbon is apparent.

In catalyst testing with the phosgene-ethylene epoxide, it was necessary to use a solvent because of the volatility of the ethylene oxide. Since 2-chloroethyl chloroformate, the reaction product, boils at 155° C., it was the logical choice. In these tests a 15% excess of phosgene was used. However, the results still showed the outstanding value of activated carbon, as shown in Table II. The reaction temperatures were from 0° to 15° C. but the clean up of the reaction was similar to that described above. Tables III and IV demonstrate the superiority of carbon catalyst with allylglycidil ether and phenyl glycidyl ether. In all cases the carbon used was a catalyst grade activated carbon (200 mesh PW grade from Columbia Carbon, Div. of Union Carbide, and 4/6 mesh pellets JXC grade from the same source). Having established the superiority of activated carbon as a catalyst and circulating product as a heat sink, tests were carried out to devise continuous operation. A large flask was used as a reservoir underneath a glass column packed with 4-8 mesh activated carbon granules. A controlled-volume pump pumped a flow of preformed chloroformate up through a heat exchanger to the top of the glass catalyst tower. There, it dissolved and mixed with an incoming feed of propylene epoxide and phosgene and fell immediately upon the catalyst. Product could either be accumulated in the bottom flask or removed continuously from the pump line.

The feed and re-circulation ratios were varied to find the optimum mixtures as well as the overall reaction rate. Temperatures were measured in the catalyst bed at top and bottom. It was found that temperatures above 115° C. were marginally harmful to yield and quality, and that temperatures over 125° C. were definitely harmful, producing hydrogen chloride gas, water and other undesired products. A catalyst charge of 88 grams of carbon was used without a change in activity to make over 10 kilos of 2-chloroisopropyl chloroformate.

Table I

| Propylene Epoxide Catalyst Tests | | | |
|---|---|---|---|
| Catalyst | Catalyst Weight | 2-chloro-isopropyl Wt. Yield % | Chloro-formate Purity % |
| None | 0 | 18.1 | 87.4 |
| Carbon | 2.5 gr | 97.5 | 95.8 |
| HCl (Anh.) | 3.6 gr | 64.3 | 84.0 |

Table I-continued

| Propylene Epoxide Catalyst Tests | | | |
|---|---|---|---|
| Catalyst | Catalyst Weight | 2-chloro-isopropyl Wt. Yield % | Chloro-formate Purity % |
| Propylene Chlorohydrin | 5.0 gr | 67.7 | 90.9 |
| $V_2O_5$ Vanadium Pentoxide | 2.5 gr | 59.9 | 91.1 |
| Glacial Acetic A. | 1.0 gr | 59.8 | 82.3 |
| Cuprous Chloride | 2.5 gr | 59.8 | 89.1 |
| Copper Metal | 2.5 gr | 16.2 | 87.2 |
| Cupric Chloride | 2.5 gr | Decomposed | |
| Cuprous Oxide | 2.5 gr | 12.4 | 88.7 |
| Silver Chloride | 2.5 gr | 40.7 | 89.2 |
| Molybdic Acid | 2.5 gr | 37.5 | 60.3 |
| Silica Gel | 2.5 gr | 16.2 | 88.8 |

Table II

| Ethylene Epoxide Catalyst Tests | | | |
|---|---|---|---|
| Catalyst | Catalyst Weight | 2 Chloro-ethyl Wt. Yield % | Chloro-formate Purity % |
| None | 0 | 23.4 | 95.0 |
| Carbon | 1 gr | 95.1 | 99.9 |
| Ethylene Chlorohydrin | 4 gr | 93.2 | 96.2 |
| HCl (Anh.) | 3.6 gr | 87.7 | 95.6 |

Table III

| Allyl Glycidyl Ether With Phosgene | | | |
|---|---|---|---|
| | | 3-Allyloxy 1-chloroisopropyl chloroformate | |
| Catalyst | Catalyst Weight | Wt. Yield % | Purity % |
| None | 0 | 17.2 | 36.0 |
| Carbon | 5.0 gr | 99.9 | 85.5 |
| HCl (Anh.) | 7.2 | 82.9 | 84.5 |

Table IV

| Phenyl Glycidyl Ether With Phosgene | | | |
|---|---|---|---|
| Catalyst | Catalyst Weight | 3-Phenooxy 1-chloroiso-propyl Wt. Yield % | Chloroformate Purity |
| None | 0 | 21.1 | 53.4 |
| Carbon | 5.0 gr | 94.8 | 85.2 |
| HCL (Anh.) | 7.2 gr | 30.1 | 42.8 |

Table V illustrates results in a continuous flow preparation of chloropropyl chloroformate through a 22 inches long by 1 inch diameter insulated catalyst column packed with 4-8 mesh catalytic grade carbon granules. The feed was an equimolar ratio of phosgene and propylene epoxide, and all products had a purity of above 97%. As previously noted, the product chloroformate was re-circulated by a pump at a ratio varied as noted. There was no external heat transfer in the catalyst column.

Table V

| Continuous Tests | | | | |
|---|---|---|---|---|
| Test | Ratio, Recirculation to Raw Material | Production Rate Gm/Hr | Highest C. Temp. | Weight % Yield |
| 1 | 10.3 | 274 | 93 | 98.9 |
| 2 | 6.4 | 284 | 106 | 99.6 |
| 3 | 5.5 | 573 | 120 | 88.9 |
| 4 | 5.1 | 404 | 125 | 90.7 |
| 5 | 4.8 | 400 | 127 | 90.8 |
| 6 | 6.9 | 248 | 113 | 97.7 |
| 7 | 12.1 | 300 | 85 | 97.7 |

While these results are not considered definitive, it is apparent that lower dilution ratios produce higher temperatures, which reduce yield. The production rate was varied to show the value of a high dilution (# 7) to give a high rate and yield as compared to # 4 or 5 with a low dilution ratio. This was confirmed in other continuous tests when recirculation was stopped entirely, and the catalyst tower was externally cooled. A high yield could only be obtained by reducing to thru-put rate to from 85 to 132 gm/hr. a fraction of the rate achieved with recirculation. Those experiments which produce the highest temperatures, also produced the lowest yields.

In summary, it is felt that Tables I-IV establish activated carbon as a superior catalyst for the reaction of phosgene and epoxides generally. It is further felt that Tables I-IV establish industrial utility for the production of 2-chlorethyl and 2-chloroisopropyl chloroformates using the noted catalyst, in a solvent of preformed product, at temperatures in the range of 60° to 125° C. A recirculation ratio of at least 4 is necessary and 7 is preferred though no limits on same have been established.

Various changes in the details, steps, materials and arrangements of parts, which have been herein described and illustrated in order to explain the nature of the invention, may be made by those skilled in the art within the principle and scope of the invention as defined in the appended claims.

What is claimed is:

1. A continuous process for the production of chlorine-substituted chloroformates from phosgene and 1-2 epoxy ring compounds comprising;

establishing a circulating stream of said chloroformate;
    passing said stream through a catalyst bed of activated carbon;
    injecting said phosgene and an epoxy compound selected from the group consisting of propylene epoxide, ethylene epoxide, allyl glycidal ether and phenyl glycidal ether into said stream ahead of said catalyst; and
    drawing off chloroformate as product.

2. The process as claimed in claim 1, wherein temperature in said bed is in the range of 60° to 125° C.

3. The process as claimed in claim 1, wherein the ratio of preformed chloroformate to reactants is at least 4:1.

4. In the process for manufacture of chlorine-substituted chloroformates by reaction of phosgene with 1-2 epoxy ring compounds selected from the group consisting of propylene epoxide, ethylene epoxide, allyl glycidal ether and phenyl glycidal ether, the improvement comprising carrying out said reaction in the presence of activated carbon as catalyst.

5. The process as claimed in claim 4, wherein reactants a maintained at a temperature in the range of 60° to 125° C.

6. The process as claimed in claim 5, wherein said temperature is maintained by carrying out said reaction in a large quantity of preformed chloroformate product as a heat absorber.

7. The process as claimed in claim 6, wherein the ratio of preformed chloroformate to reactants is at least 4:1.

* * * * *

UNITED STATES PATENT AND TRADEMARK OFFICE
CERTIFICATE OF CORRECTION

PATENT NO. : 4,120,888
DATED : 17 October 1978
INVENTOR(S) : Franklin Anderson Bolth It is certified that error appears in the above-identified patent and that said Letters Patent are hereby corrected as shown below:

Column 1, line 26: Delete "plaqued" and insert -- plagued --.

Column 6, line 23: Delete "a" (first occurrence) and insert -- are --.

Signed and Sealed this

Sixth Day of February 1979

[SEAL]

Attest:

RUTH C. MASON
Attesting Officer

DONALD W. BANNER
Commissioner of Patents and Trademarks